(12) United States Patent
Smith

(10) Patent No.: US 8,641,633 B2
(45) Date of Patent: *Feb. 4, 2014

(54) PRESSURE WIRE ASSEMBLY

(75) Inventor: Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/534,653

(22) Filed: Jun. 27, 2012

(65) Prior Publication Data

US 2012/0271178 A1  Oct. 25, 2012

Related U.S. Application Data

(63) Continuation of application No. 11/902,805, filed on Sep. 25, 2007, now Pat. No. 8,216,151.

(51) Int. Cl.
*A61B 5/02* (2006.01)
*A61M 25/00* (2006.01)

(52) U.S. Cl.
USPC .......................... 600/485; 600/486; 600/585

(58) Field of Classification Search
USPC ................... 600/485–488, 561, 585
See application file for complete search history.

(56) References Cited

U.S. PATENT DOCUMENTS

| | | | |
|---|---|---|---|
| 5,568,815 A | 10/1996 | Raynes et al. | |
| 6,152,885 A * | 11/2000 | Taepke | 600/561 |
| 6,585,660 B2 | 7/2003 | Dorando et al. | |
| 6,650,939 B2 | 11/2003 | Taepke et al. | |
| 6,926,674 B2 | 8/2005 | Tenerz et al. | |
| 2001/0039437 A1* | 11/2001 | Taepke et al. | 607/27 |
| 2002/0173724 A1* | 11/2002 | Dorando et al. | 600/486 |
| 2003/0216621 A1 | 11/2003 | Alpert | |
| 2007/0142727 A1 | 6/2007 | Zhang et al. | |

FOREIGN PATENT DOCUMENTS

| | | |
|---|---|---|
| EP | 1774905 | 4/2007 |
| WO | WO 99/55225 A1 | 11/1999 |
| WO | WO 00/12004 A1 | 3/2000 |
| WO | WO 2005/086753 A2 | 9/2005 |
| WO | WO2007/058826 A | 5/2007 |

* cited by examiner

*Primary Examiner* — Patricia Mallari
*Assistant Examiner* — Christian Jang
(74) *Attorney, Agent, or Firm* — Foley & Lardner LLP

(57) ABSTRACT

A pressure sensor wire assembly measures pressure inside a body of a patient. The assembly comprises a pressure sensor element for measuring pressure and to generate a pressure sensor signal representative of the pressure, and a pressure sensor wire having the pressure sensor element at its distal portion, and adapted to be inserted into the body in order to position the sensor element within the body. A sensor signal adapting circuitry is an integrated part of the assembly, wherein the pressure sensor signal is applied to the adapting circuitry which is adapted to automatically generate an output pressure signal, related to the sensor signal, in a standardized format such that the measured pressure is retrievable by an external physiology monitor. The assembly further comprises an external pressure sensor to measure the pressure outside the patient's body and to generate external pressure values in dependence thereto.

14 Claims, 4 Drawing Sheets

PRESSURE WIRE ASSEMBLY

CROSS REFERENCE TO RELATED APPLICATIONS

Figure 1:
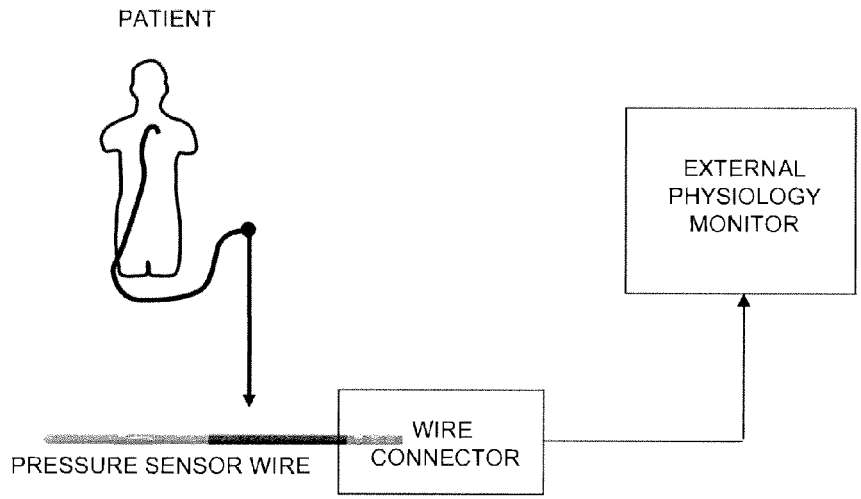

This application is a continuation of U.S. application Ser. No. 11/902,805, filed Sep. 25, 2007, now U.S. Pat. No. 8,216,151, the entire contents of which is incorporated herein by reference.

FIELD OF THE INVENTION

The present invention relates to an assembly according to the preamble of the independent claim.

BACKGROUND OF THE INVENTION

A sensor wire assembly is known from EP-1,774,905 assigned to the assignee of the present application for measuring a physiological variable, in particular pressure, inside a patient's body. The pressure sensor used in the EP-document is a miniaturized semiconductor sensor and one purpose of the assembly of EP-1,774,905 is to handle the electrical configurations of these miniaturized semiconductor sensors that are not always compatible with the transducer amplifiers in existing patient monitors. For instance, the miniaturized sensors often cannot operate over the entire range of excitation signal magnitudes and frequencies found among the various types of patient monitors. Thus, they cannot be connected directly to many of the patient monitors already in use. To be used with such existing monitors, a specialized interface must be placed between the sensor and the monitor. Such an arrangement necessitates additional circuitry on the interface and, because existing monitors have been designed to provide only limited amounts of power, the additional circuitry may require an independent source of electrical power. As a consequence, use of the newer miniaturized sensors often adds cost and complexity to the overall system.

In addition, because of the above limitations, these sensors must often be configured to generate an output signal which is proportional to the pressure sensed, but that is not related to the excitation signal, supplied to the sensor by the monitor, in a way that is directly usable by the physiology monitor, e.g. the sensitivity may be different. As discussed, this does not conform with the electrical format required by the many monitors that are commercially available and already in widespread use. As such, the newer sensors can only be used with specific signal conditioning and displaying units, thereby requiring additional equipment to be purchased. This is especially undesirable given the cost sensitivities so prevalent in today's health care environment.

U.S. Pat. No. 5,568,815 discloses an interface circuit for interfacing a sensor to a patient monitor. The interface circuit includes a power supply circuit that receives an excitation power signal generated by the patient monitor, and derives therefrom unregulated and regulated supply voltages for use by the electrical components on the interface circuit. Further, the power supply circuit generates an appropriate sensor excitation signal. The interface circuit further includes receiving circuitry for receiving a sensor output signal generated by the sensor. A scaling circuit then scales that signal into a parameter signal that is proportional to the physiological condition detected by the sensor, and that is also proportional to the excitation power signal generated by the patient monitor. An obvious drawback of the device of U.S. Pat. No. 5,568,815 is that, in order to connect the sensor to the monitor, a separate additional unit in the form of the interface circuit is required.

A similar solution is disclosed in U.S. Pat. No. 6,585,660 that relates to a signal conditioning device that interfaces a variety of sensor devices, such as guide wire-mounted pressure sensors, to physiology monitors. The signal conditioning device includes a processor for controlling a sensor excitation and signal conditioning circuitry within the signal conditioning device. The processor also supplies signals to an output stage on the signal conditioning device representative of processed sensor signals received by a sensor interface of the signal conditioning device. Power for the signal conditioning device processor is supplied by an excitation signal received from a physiology monitor that drives the output stage. In addition, a temperature compensating current source provides an adjustment current to at least one of a pair of resistive sensor elements to compensate for differences between temperature change upon the pair of resistive sensor elements, thereby facilitating nullifying temperature effects upon the resistive sensor elements.

The Association for the Advancement of Medical Instrumentation ("AAMI") has defined power requirements for physiology monitors and in particular the input/output connector to a sensor wire assembly must comply with the standard set by American National Standards Institute ("ANSI")/AAMI BP22-1994 (referred to as "BP22" in the following).

According to the BP22-standard, an input/output connector arranged at the proximal end of a five line connector cable includes a pair of differential output signal lines. The output signal lines are driven by a sensor adapting circuitry's output digital to analog converters (discussed further herein below). The differential output signal, by way of example, operates at $5\,\mu V/mmHg/V_{EXC}$. An operation range of $-150\,\mu V/V$ to $1650\,\mu V/V$ therefore represents a sensed pressure range of $-30$ to $330\,mmHg$. An exemplary resolution (minimum step) for the differential output signal is 0,2 mmHg.

A pressure measurement procedure when a pressure wire provided with a pressure sensor at its distal end is inserted into a patient's blood vessel, e.g. into the cardiac veins of the heart to measure local constrictions may last for several hours. The inventor has noted that variations and changes of the environmental air pressure in the operation room may have considerable impact on calculations based upon the measurement results received from the pressure sensor at the pressure wire inside the body in relation to environmental air pressure, which in particular may be significant if measurements are to be performed for longer time periods, e.g. several hours.

In order to fully appreciate the present invention a short background of the entire measurement procedure will be presented.

One important application of a pressure sensor wire is to be able to identify constrictions of coronary vessels, e.g. in the great cardiac vein, by performing so-called Fractional Flow Reserve-measurements (FFR). In short FFR is determined by obtaining the ratio between the pressure distally and proximally of a constriction. In practice a catheter is initially inserted and positioned with its distal part e.g. in the aorta. The distal part of the catheter is provided with a pressure sensor of a conventional type having a sensor typically positioned external to the patient's body and placed in fluid communication with the body cavity where the distal part of the catheter is positioned via a fluid-filled catheter line. Pressure variations within the body cavity are then indirectly communicated to the diaphragm at the pressure sensor by way of fluid contained in a lumen running within the entire catheter length and having a distal opening close to the distal end of the catheter. As such, the accuracy of such systems has suffered due to variations in hydrostatic pressure and other inconsistencies associated with the fluid column.

When the catheter is correctly positioned, the pressure sensor wire is inserted into another lumen of the catheter and advanced until the pressure sensor at the distal end of the pressure sensor wire is in, or close to, the distal opening of the lumen. The calibration of the pressure sensor of the pressure sensor wire in relation to the pressure measured by the catheter pressure sensor is then performed. When the calibration has been performed the pressure sensor wire is further advanced until its pressure sensor element is positioned distally of the constriction, and the assembly is then ready to measure the pressures and determine FFR.

Since the pressure sensor element is calibrated to the ambient pressure at the start of the measurement procedure, changes of the ambient pressure during the procedure may have significant effect of the accuracy of the calculated FFR as the measured catheter pressure reflects these changes whereas the pressure from the calibrated pressure sensor element does not. Thus, the catheter pressure sensor measures pressure in relation to the ambient pressure, whereas the pressure sensor of the pressure sensor wire measures the absolute pressure. During the calibration process the pressure sensor wire pressure is set equal to the catheter pressure sensor pressure.

Thus, the object of the present invention is to achieve an improved pressure sensor assembly that generates reliable pressure measurement values irrespectively of external pressure variations, and that is easy to use and has a low over all cost.

SUMMARY OF THE INVENTION

The above-mentioned object is achieved by the present invention according to the independent claim.

Preferred embodiments are set forth in the dependent claims.

According to the invention a pressure monitoring sensor, i.e. a barometer, measures external pressure when the procedure of determining the internal pressure is initiated and determines a compensation value based upon the initial external pressure value and the present value, in order to compensate for pressure variation occurring during the whole procedure. A pressure difference value is determined by determining the difference between the present pressure value, i.e. the pressure value present when the pressure measurement is performed, and the initial pressure value and the measured internal pressure value is then compensated by the pressure difference value.

SHORT DESCRIPTION OF THE APPENDED DRAWINGS

FIG. 1 schematically illustrates the present invention according to a first embodiment.

Figure 2:
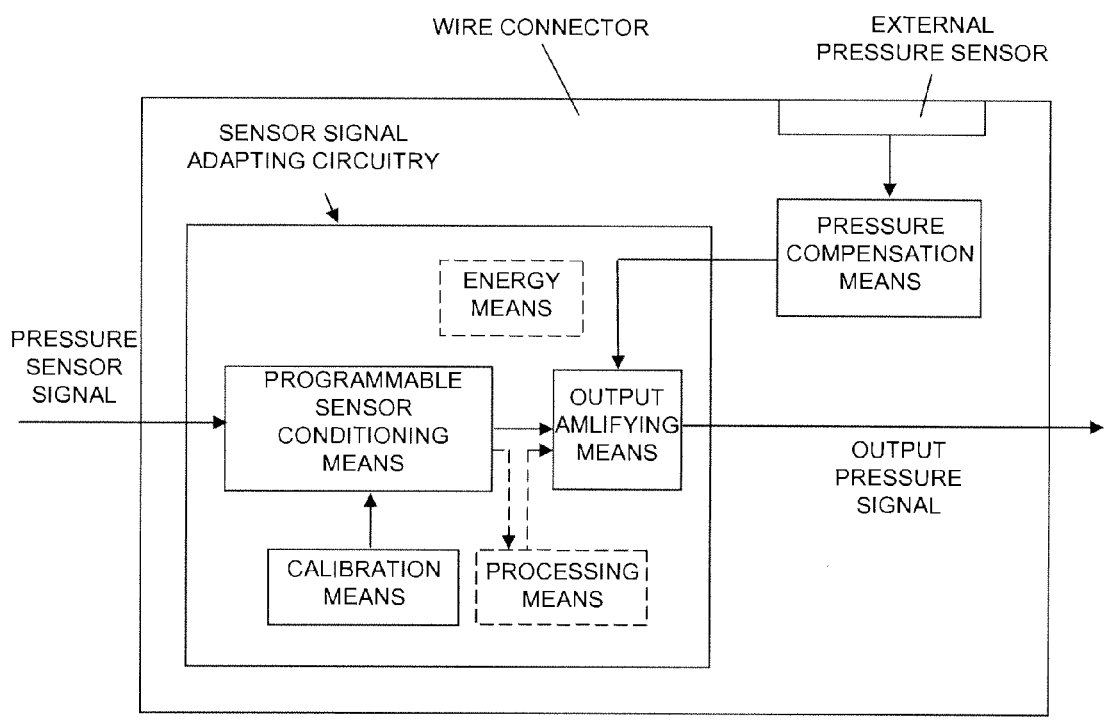

FIG. 2 schematically shows a block diagram of the wire connector of the first embodiment of the present invention.

Figure 3:
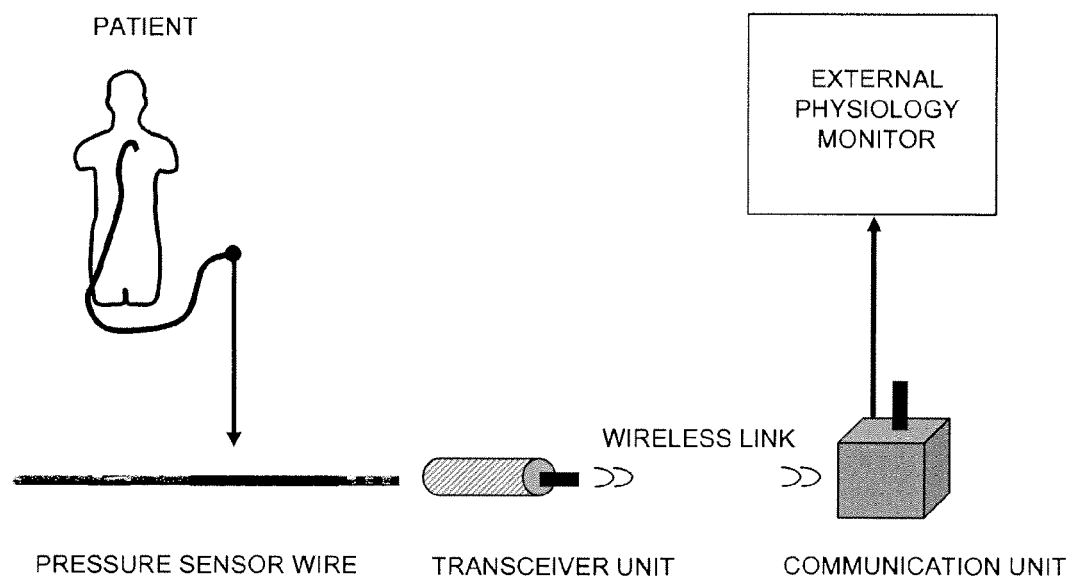

FIG. 3 schematically illustrates the present invention according to a second and a third embodiments.

Figure 4:
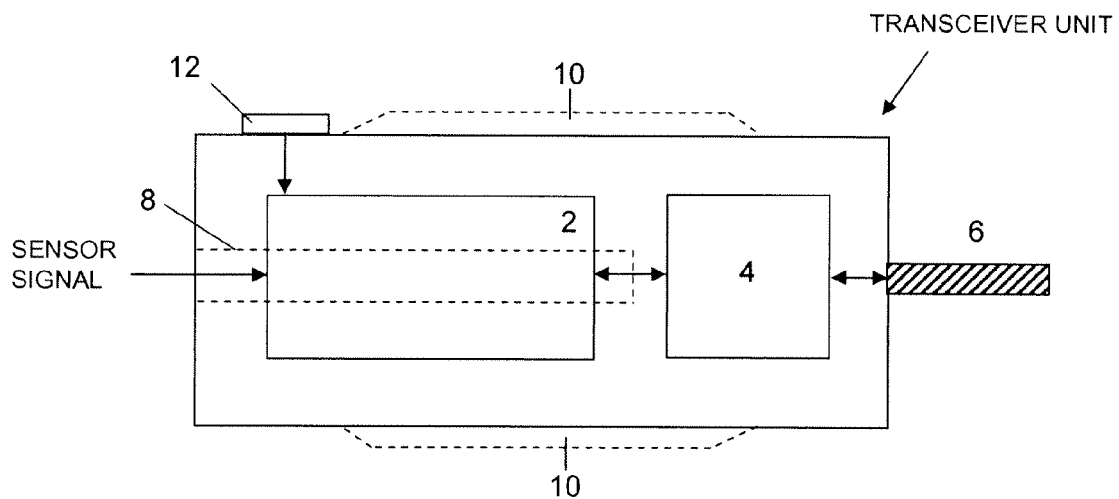

FIG. 4 schematically shows the transceiver unit of the second or third embodiment of the present invention.

Figure 5:
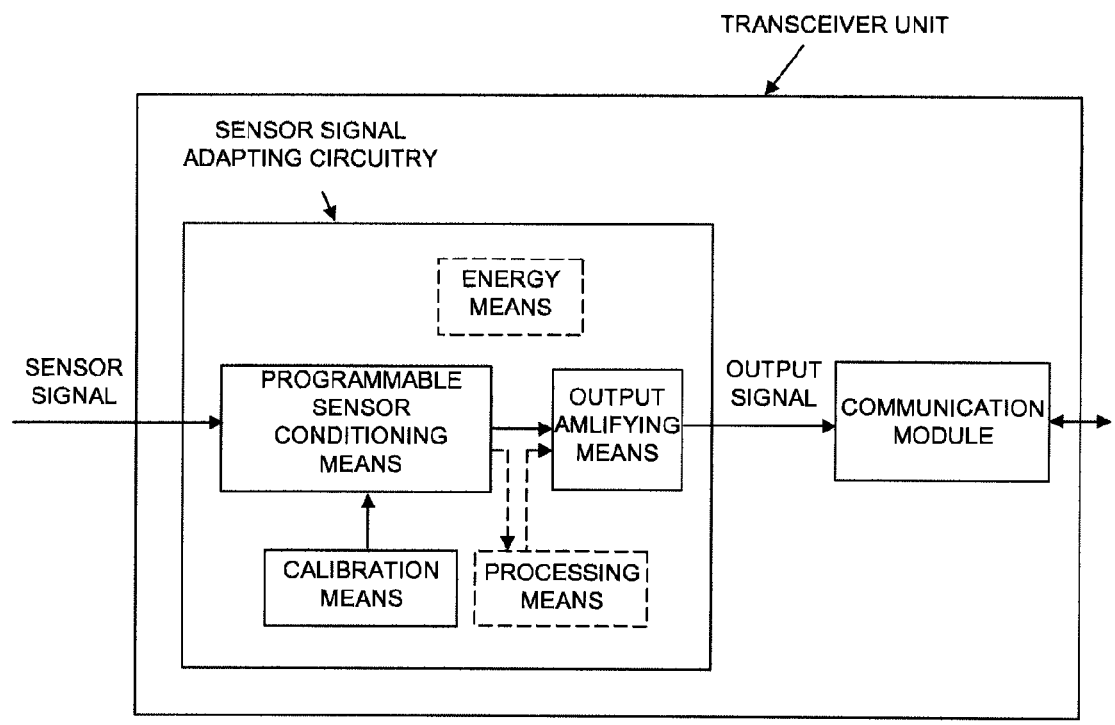

FIG. 5 schematically shows a block diagram of the transceiver unit of the second embodiment of the present invention.

Figure 6:
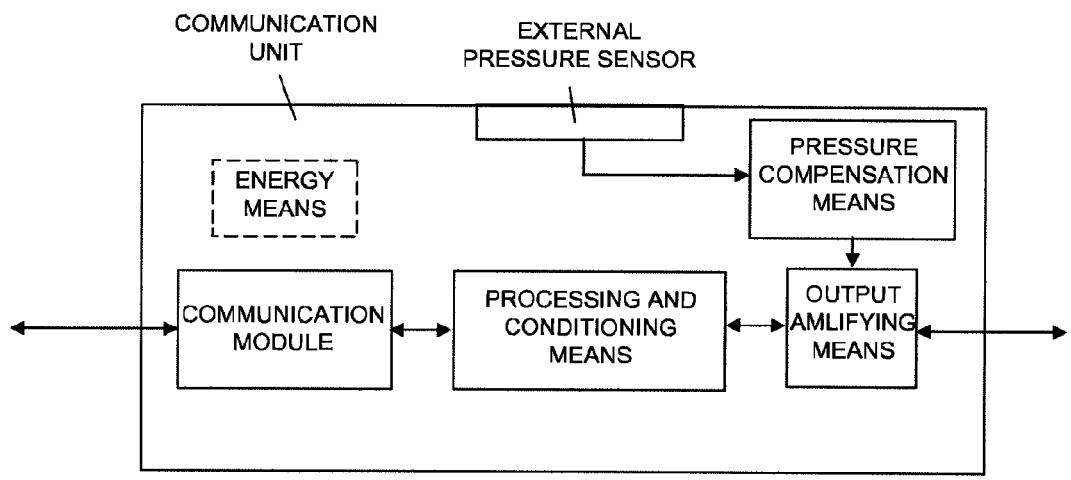

FIG. 6 schematically shows a block diagram of the communication unit of the second embodiment of the present invention.

Figure 7:
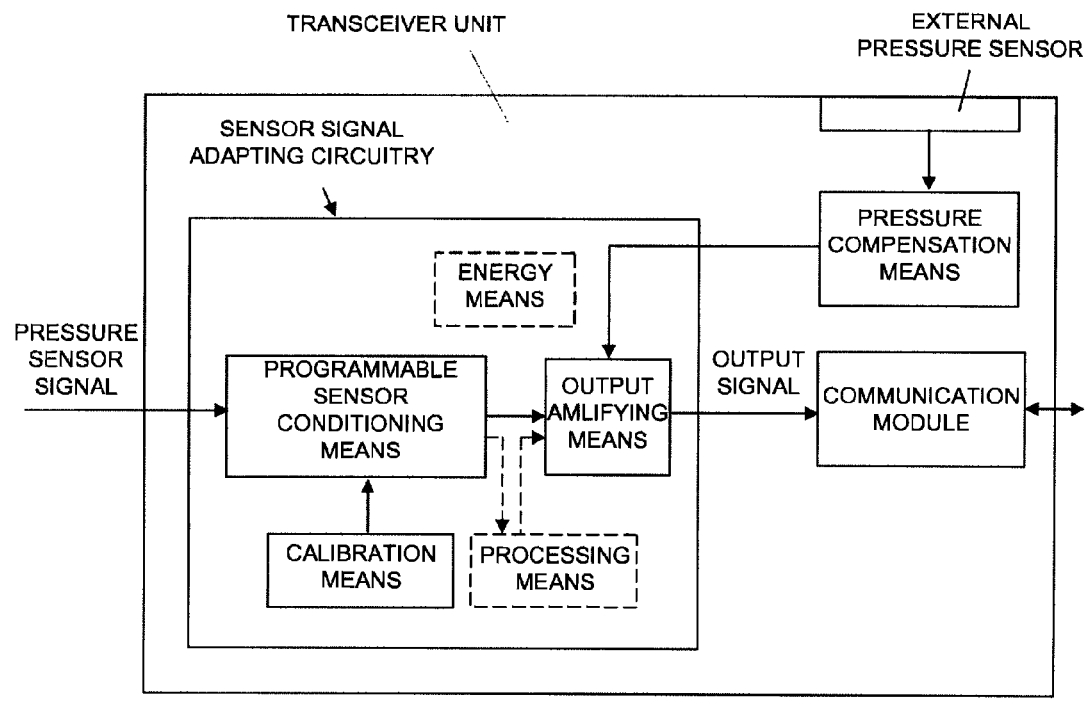

FIG. 7 schematically shows a block diagram of the transceiver unit of the third embodiment of the present invention.

Figure 8:
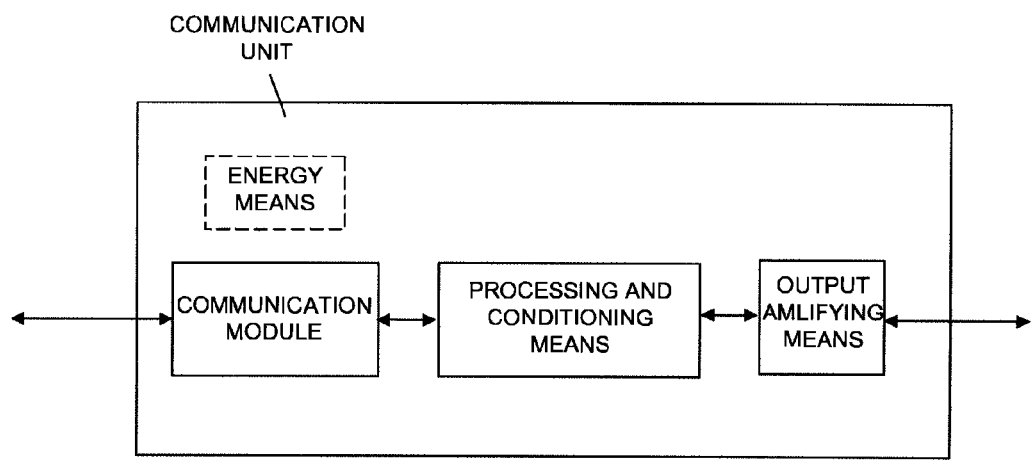

FIG. 8 schematically shows a block diagram of the communication unit of the third embodiment of the present invention.

DETAILED DESCRIPTION OF PREFERRED EMBODIMENTS OF THE INVENTION

FIG. 1 schematically illustrates a pressure sensor wire assembly for measuring pressure in a body of a patient, and FIG. 2 shows a block diagram schematically illustrating a wire connector according to a first embodiment of the present invention.

With references to FIG. 2 the present invention relates to a pressure sensor wire assembly for measuring pressure inside a body of a patient. The assembly comprises a pressure sensor element, not shown in the figure, for measuring pressure and to generate a pressure sensor signal in response of the measured pressure, a pressure sensor wire (FIG. 1) having the pressure sensor element at its distal portion, and adapted to be inserted into the body of a patient in order to position the sensor element within the body. The assembly further comprises a sensor signal adapting circuitry, being an integrated part of the assembly, wherein the pressure sensor signal is applied to the adapting circuitry that is adapted to automatically generate an output pressure signal, related to the pressure signal, in a standardized format such that the measured pressure is retrievable by an external physiology monitor (FIG. 1). The sensor signal adapting circuitry comprises a programmable sensor conditioning unit, a calibration unit, being a storage means into which calibration data may be supplied, stored and altered, e.g. an electrically erasable programmable read-only memory (EEPROM), energy means and an output amplifying unit.

The programmable sensor conditioning unit is preferably a PGA309 programmable analog sensor conditioner (available from Texas Instruments Inc.) specifically designed for bridge sensors. The PGA309 is particularly designed for resistive bridge sensor applications and contains three main gain blocks for scaling differential input bridge sensor signals. Hence, as discussed in the above, a signal representing the measured physiological variable may be adapted such that a signal in a format expected by the monitor is provided. This signal format is determined by the reference voltage supplied to the sensor signal adapting circuitry and the actual value of the signal measured by the sensor. The PGA309 can be configured for use with an internal or external voltage reference. According to the present invention, an internal reference voltage of e.g. +2,5V is supplied to the PGA309 from the energy means.

Thus, the conditioning means generates an analog output voltage signal related to the sensor signal such that the measured physiological variable, i.e. the pressure, may be retrieved by the external device.

Since each sensor element is an individual item with its own characteristics, each sensor assembly comprises a calibration means, preferably an electrically erasable programmable read-only memory (EEPROM) which contains individual calibration data obtained during calibration of the sensor element performed for each individual sensor wire assembly. The calibration is performed in connection with manufacture of the pressure sensor wire. Calibration data takes into account parameters such as voltage offsets and temperature drift, etc.

The bridge pressure sensor is preferably energized from the PGA309 via an excitation voltage $V_{EXC}$, generated by the PGA309 circuit. As an alternative the pressure sensor may be energized from a separate energy source, e.g. a battery or a capacitor means, or from an external power supply, e.g. an external mains supply via the monitor.

For a given excitation voltage $V_{EXC}$, e.g. generated by the PGA309 circuit, the output voltage ($V_{IN1}-V_{IN2}$) of the bridge is a voltage proportional to the pressure applied to the sensor. Hence, the sensor output voltage ($V_{IN1}-V_{IN2}$) (sensor signal in FIG. 2) of the bridge is proportional to the pressure applied to the sensor, which for a given pressure will vary with the applied excitation voltage. This sensor output voltage is preferably compensated for temperature variation at the site of the sensor and the compensated sensor output voltage is applied to the PGA309 circuit. The PGA309 circuit also includes gain blocks for adjusting the output signal from that circuit and are used in addition to the output amplifying means mentioned above.

According to another preferred embodiment a processing means, preferably a microprocessor (e.g. a PIC16C770 or a nRF24E1, shown with dashed lines in FIG. 2) may further be employed to process and adapt the analog output voltage $V_{OUT}$ of the conditioned sensor, which output voltage is supplied via the PGA309 programmable analog sensor conditioner. The analog output signal from the PGA309 circuit is A/D-converted prior to being applied to the processing means. To adapt the sensor signal to the BP22 signal standard, it may be necessary to process the sensor signal further before it is applied to the physiology monitor. For instance a multiplying digital-analog converter (DAC) which possibly is comprised in the processing means is supplied with digital data (e.g. a 12-bit word) representing the signal measured by the sensor element and the reference voltage.

The assembly further comprises an external pressure sensor arranged at the assembly to measure the pressure outside the patient's body and to generate external pressure values in dependence thereto. The external pressure values are applied to a pressure compensation means, in the assembly, adapted to generate a compensation value reflecting the external pressure variation during a measurement procedure, and the output pressure signal is compensated by the compensation value prior to the output pressure signal being applied to the external physiology monitor.

A person skilled in the art of the pressure sensors will be able to identify numerous pressure sensors applicable as external pressure sensors to be used in the pressure wire assembly according to the present invention. In the following two exemplary sensors will be described.

The external pressure sensor may be a SCP1000-D01/D11 digital absolute pressure sensor by VTI Technologies, intended for barometric pressure measurement and altimeter applications for 30 kPa . . . 120 kPa and −20° C . . . 70° C. measuring ranges. The pressure and temperature output data is calibrated and compensated internally and the communication between the SCP1000 and its host micro-controller is realized using SPI or I²C interfaces. SCP1000 is comprised of a VTI's 3D MEMS capacitive sensing element, a dedicated low power CMOS interface ASIC with on-chip calibration memory, 4 preset measuring modes and a LCP (Liquid Crystal Plastic) MID (Molded Interconnect Device) housing. The component is a surface mountable device incorporating a circular vertical wall for easy waterproof sealing.

Another applicable sensor is a pressure sensor by Honeywell Sensing and Control, Inc. in the 24PC Series that contain sensing elements that consist of four piezoresistors buried in the face of a thin, chemically-etched silicon diaphragm. A pressure change causes the diaphragm to flex, inducing a stress in the diaphragm and the buried resistors. The resistor values change in proportion to the stress applied and produce an electrical output. These sensors are small, low cost and reliable. They feature excellent repeatability, high accuracy and reliability under varying environmental conditions. In addition, they feature highly consistent operating characteristics from one sensor to the next, and interchangeability without recalibration.

When a measurement procedure is initiated an initial external pressure value is determined as being the external pressure value measured initially, and the compensation means is adapted to generate the compensation value in relation to the difference between the present value and the initial external pressure value. Thus, each time a measurement is performed, i.e. for each pressure value obtained by the pressure sensor wire and generated by the assembly during a measurement procedure, the pressure value is compensated for any variation of the external pressure by adding or subtracting the pressure value by the compensation value.

According to a first embodiment of the present invention the assembly comprises a wire connector, see FIG. 2, to which a proximal portion of the pressure sensor wire is adapted to be connected. The wire connector is in turn connected to the external physiology monitor via a connecting cable, not shown in FIG. 2. The wire connector includes the above-mentioned sensor signal adapting circuitry.

The external pressure sensor is preferably arranged in the wire connector, but may alternatively be arranged along the connecting cable.

The pressure compensation means comprises a control means and a storage means, not shown in the figures, and the generated external pressure values are stored in said storage means prior to being used by the control means to determine the compensation value.

FIG. 3 schematically illustrates the present invention according to a second and a third embodiment where the assembly comprises a transceiver unit and a communication unit. The pressure sensor wire is adapted to be connected, at its proximal end, to the transceiver unit that is adapted to wirelessly communicate via a communication signal with the communication unit, and the communication unit is in turn connected to the external physiology monitor, in order to transfer the output pressure signal to the external physiology monitor.

FIG. 4 schematically shows the transceiver unit of the second or third embodiment of the present invention.

The second and third embodiments, where the communication signal is a radio frequency signal, will now be described in detail. The wireless communication is performed by using an established communication protocol, e.g., BLUETOOTH®. Although the transceiver unit and the communication unit are described in connection with the use of a radio frequency signal it should be appreciated that relevant features would be equally applicable in case any alternative communication signals are used, e.g. optical or magnetic signals.

With references to FIGS. 3 and 4, the communication module is connected to an antenna 6. In the figures the antenna is illustrated as protruding outside the transceiver unit but may, as in an alternative, be integrated into the housing of the transceiver unit. The pressure sensor wire is adapted to be inserted into an elongated aperture 8 of the transceiver unit. The aperture is at its inner surface provided with a number of electrical connecting surfaces (not shown) to be connected to electrode surfaces at the proximal end of the pressure sensor wire when inserted into the aperture 8. The transceiver unit is further provided with wire fastening means (not shown) to firmly fixate the wire when correctly inserted into the aperture.

According to a preferred embodiment the transceiver unit is adapted to receive the proximal end to the pressure sensor wire having an outer diameter of 0,35 mm, i.e. the inner diameter of the elongated aperture 8 is slightly larger than 0,35 mm.

When the pressure sensor wire is fixated to the transceiver unit the unit may be used as a torque device when guiding the pressure sensor wire during insertion into a patient. Preferably the transceiver unit is provided with guiding means 10, e.g. in the form of one or many elongated ribs on the outer surface of the transceiver unit, or by providing the transceiver unit with a roughened surface.

The pressure sensor wire may be fixated to the transceiver unit such that as the transceiver unit is rotated along its longitudinal axis the sensor wire is also rotated, which often is necessary in order to guide the sensor wire during the insertion procedure. As an alternative, the sensor wire is fixated to the transceiver unit in such way that the sensor wire may be rotated in relation to the transceiver unit. The rotation of the sensor wire is then achieved by firmly holding the transceiver unit by one hand and by rotating the sensor wire by the other hand.

The transceiver unit is preferably activated and initiated via an activation button 12 arranged at the housing of the unit. The activation button is preferably mechanically activated.

The transceiver unit comprises energy means to energize the transceiver unit and the circuitry of the connected pressure sensor wire. The energy means is preferably a battery or a capacitor that e.g. may be included in the sensor signal adapting circuitry.

The pressure sensor wire as well as the transceiver unit are preferably disposable units that should be possible to sterilize prior to use.

The transceiver unit comprises a first communication module to handle the radio frequency communication with the communication unit that is provided with a second communication module (see FIGS. 6 and 8).

When the pressure sensor wire has been inserted into the transceiver unit and the communication unit is connected to the external device the system is ready for use. By pressing the activation button on the transceiver unit it is activated and will then try to establish a radio link connection with the communication unit. This is preferably performed by a conventional handshake procedure in order to identify the transceiver unit. The system is now ready to receive measured sensor data.

The second and third embodiments of the present invention differs from each other in that in the second embodiment the external pressure sensor and the pressure compensation means are arranged in the communication unit, and in the third embodiment the external pressure sensor and the pressure compensation means are arranged in the transceiver unit.

Thus, FIGS. 5 and 6 schematically show block diagrams of the transceiver unit and of the communication unit, respectively, of the second embodiment of the present invention, and FIGS. 7 and 8 schematically show block diagrams of the transceiver unit and of the communication unit, respectively, of the third embodiment of the present invention.

With regard to the common features and function of the sensor signal adapting circuitry of the first, second and third embodiments it is referred to the description in connection with FIG. 2.

In the second and third embodiments the adaptation of the sensor signal to the standard, e.g. BP22 signal standard, is performed in the transceiver unit, and in particular in the sensor signal adapting circuitry (see FIGS. 5 and 7). However, this adaptation, in its entirety or only in parts, may, as an alternative, instead be performed by a corresponding circuitry arranged in the communication unit. These embodiments are schematically illustrated in FIGS. 6 and 8. The wirelessly transmitted pressure sensor values would then be in the form of "raw" measured data that would be conditioned by a processing and conditioning means in the communication unit in order to be in a correct format to be supplied to the external system according to a prescribed standard format.

Thus, the second embodiment is illustrated by FIGS. 5 and 6, where the processing and conditioning means should be omitted in FIG. 6. An alternative second embodiment is illustrated by FIGS. 5 and 6 where instead the programmable sensor conditioning means should be omitted in FIG. 5.

In the second embodiment the external pressure sensor is either energized by the energy means within the communication unit, or energized via the external monitor and/or via external mains supply. The energy means may be e.g. a battery or capacitor.

Similarly, the third embodiment is illustrated by FIGS. 7 and 8, where the processing and conditioning means should be omitted in FIG. 8. An alternative third embodiment is illustrated by FIGS. 7 and 8 where instead the programmable sensor conditioning means should be omitted in FIG. 7.

In the third embodiment the external pressure sensor is energized by the energy means within the transceiver unit, preferably the same energy means the energizes the circuitry of the connected pressure sensor wire. The energy means may be e.g. a battery or capacitor.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A pressure sensor wire assembly for measuring pressure inside a body of a patient, comprising:
    a pressure sensor element configured to measure pressure and to generate a pressure sensor signal representative of the measured pressure;
    a pressure sensor wire, the pressure sensor element being located at a distal portion of the pressure sensor wire, wherein the pressure sensor wire is adapted to be inserted into the body in order to position the pressure sensor element within the body;
    a sensor signal adapting circuitry configured to receive the pressure sensor signal and automatically generate an output pressure signal, related to the pressure sensor signal, in a standardized format such that the measured pressure is retrievable by an external physiology monitor;
    an external pressure sensor configured to measure an external pressure outside the patient's body and to generate an external pressure value based on the external pressure;
    a transceiver unit; and
    a communication unit, wherein the external pressure sensor is arranged in the communication unit,
    wherein the pressure sensor wire is adapted to be connected at its proximal end to the transceiver unit,
    wherein the transceiver unit is configured as a torque device with a guiding mechanism configured to guide the pressure sensor wire during insertion into the patient, and
    wherein the communication unit is configured to be connected to the external physiology monitor in order to transfer the output pressure signal to the external physiology monitor.

2. The pressure sensor wire assembly according to claim 1,
wherein the communication unit is configured to be connected to the external physiology monitor, and
wherein said transceiver unit is adapted to wirelessly communicate via a communication signal with said communication unit to transfer the output pressure signal to the external physiology monitor.

3. The pressure sensor wire assembly according to claim 2, wherein the wireless communication is performed by using an established communication protocol.

4. The pressure sensor wire assembly according to claim 1, further comprising:
a pressure compensator configured to receive the external pressure value and to generate a compensation value reflecting external pressure variation during a measurement procedure, wherein the output pressure signal is adjusted based on the compensation value.

5. The pressure sensor wire assembly according to claim 4, wherein the output pressure signal is adjusted based on the compensation value prior to the output pressure signal being sent to the external physiology monitor.

6. The pressure sensor wire assembly according to claim 4, wherein the pressure compensator is configured to determine an initial external pressure value measured when a measurement procedure is initiated, and to generate the compensation value based on a difference between a present external pressure value and the initial external pressure value.

7. The pressure sensor wire assembly according to claim 4, wherein the pressure compensator comprises a control unit, and a storage unit configured to store the received external pressure value.

8. The pressure sensor wire assembly according to claim 4, wherein the pressure compensator is arranged in the communication unit.

9. The pressure sensor wire assembly according to claim 1, wherein the transceiver unit has an elongated aperture adapted to receive the proximal end of the pressure sensor wire.

10. The pressure sensor wire assembly according to claim 9, wherein the proximal end of the pressure sensor wire has an outer diameter of 0.35 mm, and an inner diameter of the elongated aperture is slightly larger than 0.35 mm.

11. The pressure sensor wire assembly according to claim 1, wherein the pressure sensor wire is configured to transmit the pressure sensor signal external to the body.

12. The pressure sensor wire assembly according to claim 1, wherein the guiding mechanism comprises a roughened surface on a housing of the transceiver unit.

13. The pressure sensor wire assembly according to claim 1, wherein the guiding mechanism comprises one or more elongated ribs on an outer surface of a housing of the transceiver unit.

14. The pressure sensor wire assembly according to claim 1, wherein the transceiver unit is generally cylindrical in shape.

* * * * *